United States Patent
Schumann

(10) Patent No.: US 8,108,047 B2
(45) Date of Patent: Jan. 31, 2012

(54) DEVICE AND METHOD FOR THE TREATMENT OF PAIN WITH ELECTRICAL ENERGY

(75) Inventor: Daniel H. Schumann, Laguna Niguel, CA (US)

(73) Assignee: NewLife Sciences LLC, Merrimack, NH (US)

( * ) Notice: Subject to any disclaimer, the term of this patent is extended or adjusted under 35 U.S.C. 154(b) by 926 days.

(21) Appl. No.: 11/594,389

(22) Filed: Nov. 8, 2006

(65) Prior Publication Data

US 2007/0106342 A1    May 10, 2007

Related U.S. Application Data

(60) Provisional application No. 60/735,156, filed on Nov. 8, 2005.

(51) Int. Cl.
*A61N 1/36* (2006.01)
(52) U.S. Cl. .......................................................... 607/46
(58) Field of Classification Search ................ 607/46
See application file for complete search history.

(56) References Cited

U.S. PATENT DOCUMENTS

| | | | |
|---|---|---|---|
| 4,112,923 A | 9/1978 | Tomecek | |
| 4,319,584 A * | 3/1982 | McCall | 607/136 |
| 4,714,886 A | 12/1987 | Halpern | |
| 5,109,847 A | 5/1992 | Liss et al. | |
| 5,231,354 A | 7/1993 | Leunbach | |
| 5,347,221 A | 9/1994 | Rubinson | |
| 5,505,932 A | 4/1996 | Grinstaff et al. | |
| 5,517,119 A | 5/1996 | Weinstock et al. | |
| 5,571,149 A * | 11/1996 | Liss et al. | 607/72 |
| 5,573,552 A | 11/1996 | Hansjurgens | |
| 5,592,086 A | 1/1997 | Weinstock et al. | |
| 5,674,261 A * | 10/1997 | Smith | 607/46 |
| 5,814,078 A | 9/1998 | Zhou et al. | |
| 5,865,746 A | 2/1999 | Murugesan et al. | |
| 5,900,227 A | 5/1999 | Janzen et al. | |
| 5,945,564 A | 8/1999 | Takayanagi | |
| 6,110,106 A | 8/2000 | MacKinnon et al. | |
| 6,140,346 A | 10/2000 | Andrulis, Jr. et al. | |
| 6,157,854 A | 12/2000 | Haber et al. | |
| 6,238,425 B1 | 5/2001 | Thiberg | |
| 6,242,919 B1 | 6/2001 | Zuk et al. | |
| 6,302,900 B1 | 10/2001 | Riggs | |
| 6,319,682 B1 | 11/2001 | Hochman | |
| 6,335,625 B1 | 1/2002 | Bryant et al. | |
| 6,430,430 B1 | 8/2002 | Gosche | |

(Continued)

FOREIGN PATENT DOCUMENTS

DE    2443913 A1    4/1976

(Continued)

OTHER PUBLICATIONS

Engstrom, Stefan, Resonances and Magnetic Field Detection in Biological Systems, Electricity and Magnetism in Biology and Medicine, 1999, pp. 223-226, Academic/Plenum Publishers.

(Continued)

*Primary Examiner* — George Evanisko
(74) *Attorney, Agent, or Firm* — Nixon Peabody LLP

(57) ABSTRACT

An electronic pain treatment device delivering electrical energy to the tissue of a patient in pain is provided which includes a variable wave generator, an impedance measurement circuit, and at least one electrode probe. Associated methods for treating pain are also disclosed.

21 Claims, 6 Drawing Sheets

U.S. PATENT DOCUMENTS

| | | | |
|---|---|---|---|
| 6,461,375 B1 | 10/2002 | Baudry et al. | |
| 6,465,507 B2 | 10/2002 | Tang et al. | |
| 6,495,601 B1 | 12/2002 | Hochman | |
| 6,566,874 B1 | 5/2003 | Speier et al. | |
| 6,573,063 B2 | 6/2003 | Hochman | |
| 6,594,527 B2 * | 7/2003 | Mo | 607/74 |
| 6,671,540 B1 | 12/2003 | Hochman | |
| 6,689,806 B1 | 2/2004 | Tang et al. | |
| 6,706,709 B2 | 3/2004 | Tang et al. | |
| 6,836,114 B2 | 12/2004 | Reddy et al. | |
| 6,845,262 B2 | 1/2005 | Albert et al. | |
| 6,974,415 B2 | 12/2005 | Cerwin et al. | |
| 7,010,356 B2 | 3/2006 | Jog et al. | |
| 7,082,325 B2 | 7/2006 | Hashimshony | |
| 7,150,710 B2 | 12/2006 | Haber et al. | |
| 7,198,776 B2 | 4/2007 | Klaveness et al. | |
| 7,483,734 B2 * | 1/2009 | Colthurst | 600/547 |
| 2001/0039375 A1 | 11/2001 | Lee et al. | |
| 2002/0042427 A1 | 4/2002 | Tang et al. | |
| 2002/0052369 A1 | 5/2002 | Tang et al. | |
| 2002/0055092 A1 | 5/2002 | Hochman | |
| 2003/0083724 A1 | 5/2003 | Jog et al. | |
| 2003/0130709 A1 | 7/2003 | D.C. et al. | |
| 2004/0015188 A1 * | 1/2004 | Coulter | 607/3 |
| 2005/0027333 A1 * | 2/2005 | Lennox | 607/89 |
| 2005/0165459 A1 | 7/2005 | Coulter | |
| 2005/0177201 A1 | 8/2005 | Freeman | |
| 2005/0177202 A1 | 8/2005 | Classen et al. | |
| 2007/0106342 A1 | 5/2007 | Schumann | |
| 2007/0129759 A1 * | 6/2007 | Colthurst | 607/2 |

FOREIGN PATENT DOCUMENTS

| | | | |
|---|---|---|---|
| EP | 0662311 A | | 7/1995 |
| EP | 1537893 A2 | | 6/2005 |
| WO | WO 2005/118061 | * | 12/2005 |
| WO | WO 2005/118061 A | | 12/2005 |

OTHER PUBLICATIONS

David J. Muehsam and Arthur A. Pilla. The Sensitivity of Cells and Tissues to Exogenous Fields: Dependence Upon Target System Initial State, Electricity and Magnetism in Biology and Medicine, 1999, pp. 405-408, Academic Plenum Publishers.

Arthur A. Pilla, David J. Muehsam and Marko S. Markov, A Larmor Precession/Dynamical System Model Allows uT-Range Magnetic Field Effects on Ion Binding in the Presences of Thermal Noise, Electricity and Magnetism in Biology and Medicine, 1999, pp. 395-399, Academic/Plenum Publishers.

Mitsuru Yasui, Takehiko Kikuchi, Wataru Ooba, Mayumi Obo, Shiro Konishi, and Yoshihisa Otaka, Effect of Magnetic Field Exposure on Calcium Channel Currents Using Patch-Clamp Technique, Electricity and Magnetism in Biology and Medicine, 1999, pp. 581-584, Academic/Plenum Publishers.

PCT International Search Report for International Application No. PCT/US2006/043582 dated Mar. 26, 2007 (4 pages).

PCT International Written Opinion for International Application No. PCT/US2006/043582 dated Mar. 26, 2007 (9 pages).

PCT International Search Report for International Application No. PCT/US2009/56990 dated Nov. 2, 2009 (3 pages).

PCT International Written Opinion for International Application No. PCT/US2009/56990 dated Nov. 2, 2009 (5 pages).

* cited by examiner

DEVICE AND METHOD FOR THE TREATMENT OF PAIN WITH ELECTRICAL ENERGY

PRIORITY CLAIM

This application claims the benefit of U.S. provisional patent application 60/735,156 filed Nov. 8, 2005 entitled DEVICE AND METHOD FOR THE TREATMENT OF PAIN WITH ELECTRICAL ENERGY.

FIELD OF THE INVENTION

The present invention relates to devices and methods for the treatment of pain. In particular, the present invention relates to devices and methods of treating pain via administration of specific electrical energy to trigger points.

BACKGROUND OF THE INVENTION

Pain is a major medical problem. Best estimates are that nearly 120 million Americans suffer from chronic pain; at least 10% of these individuals are in serious pain (50 mm or more on the 100 mm visual analog scale [VAS]) despite all treatment. Studies show that many pain sufferers, particularly those suffering from chronic pain, cannot be treated effectively. The effects of ineffective treatment include reduced mobility, limited function, poor sleep and low quality of life. For many, chronic pain is truly devastating.

In addition, current methods for the treatment of chronic pain often have undesirable effects. For instance, the typical oral or topical administration of a drug can result in widespread systemic distribution of the drug and undesirable side effects. Epidural blocks are of uncertain effectiveness and can be only given a limited number of times. Surgery is employed to treat many forms of pain but recent studies show outcomes are uncertain, and surgery is expensive and invasive.

Electricity has been used to treat pain for many years, starting with the ancient Egyptians who used electric eels from the Nile to treat pain. In theory, treatment of pain by electricity or electrical means could have advantages compared with current alternatives, in that it would provide relief in a non-invasive manner without side effects. Currently, Transcutaneous Electrical Nerve Stimulation (TENS) is used as a palliative treatment for pain. This technology, which inputs electricity using conductive adhesive pads over painful sites, stimulates certain nerve fibers and is theorized to close a pain "gate" between the painful site and the brain. In so doing it blocks the sensation of pain. However, once the device is turned off and the pads removed the pain "gate" opens and the sensation of pain returns. Thus TENS, while useful in treating pain in the short-term, does not have a lasting effect.

What is needed is a method of treating pain that is long-lasting, and that does not have the drawbacks of current treatment methods such as surgery, epidural blocks or drugs.

SUMMARY OF THE INVENTION

The electronic pain treatment device of the present invention, combined with its method of application, provides an effective, lasting and non-surgical means of treating pain. The electronic pain treatment device administers electrical energy, of a specific electrical waveform and generated by the device, to trigger points associated with the pain.

DETAILED DESCRIPTION OF THE INVENTION

Figure 1:
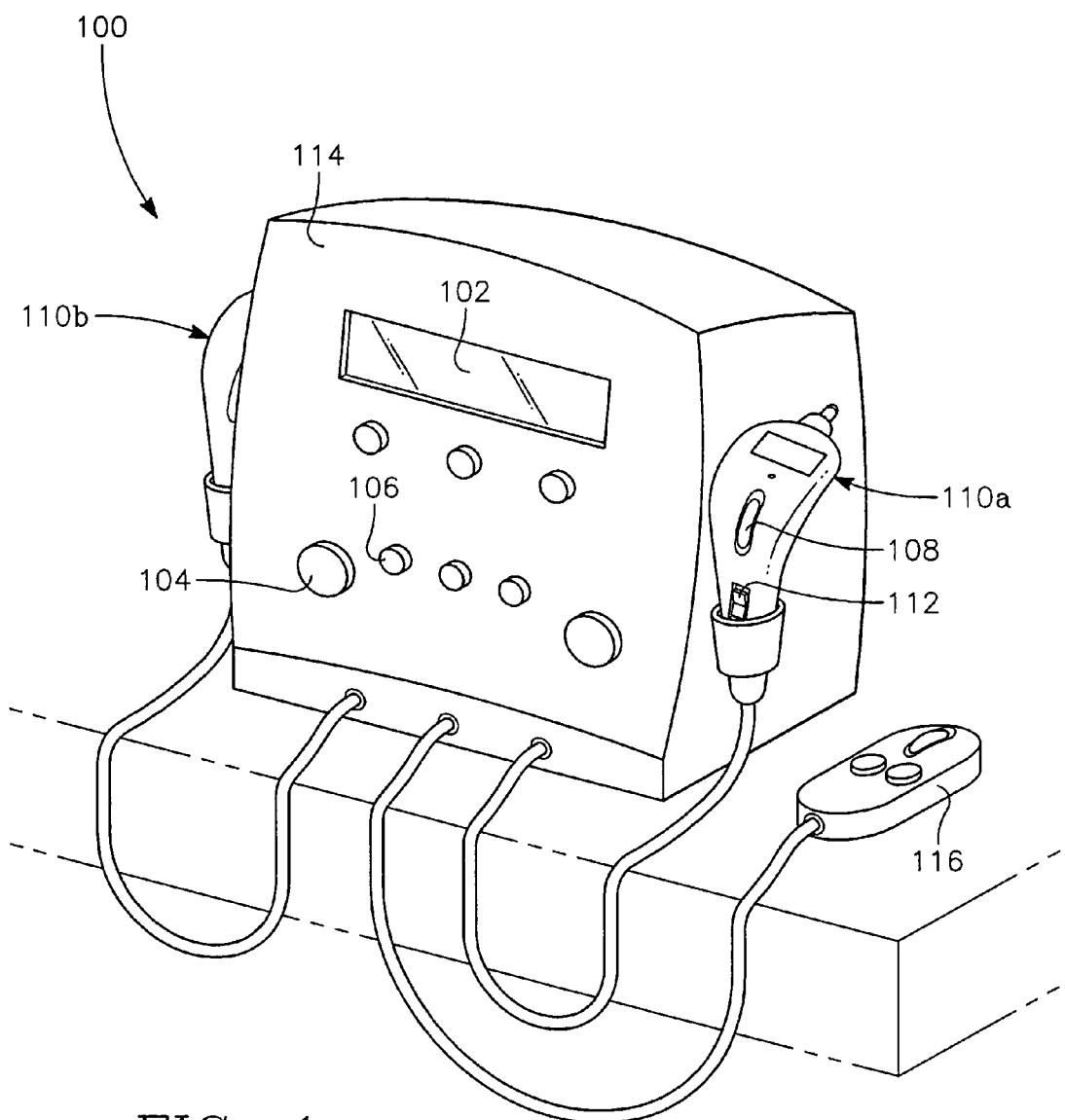
FIG. 1 depicts one embodiment of the electronic pain treatment device of the present invention.
Figure 2A:
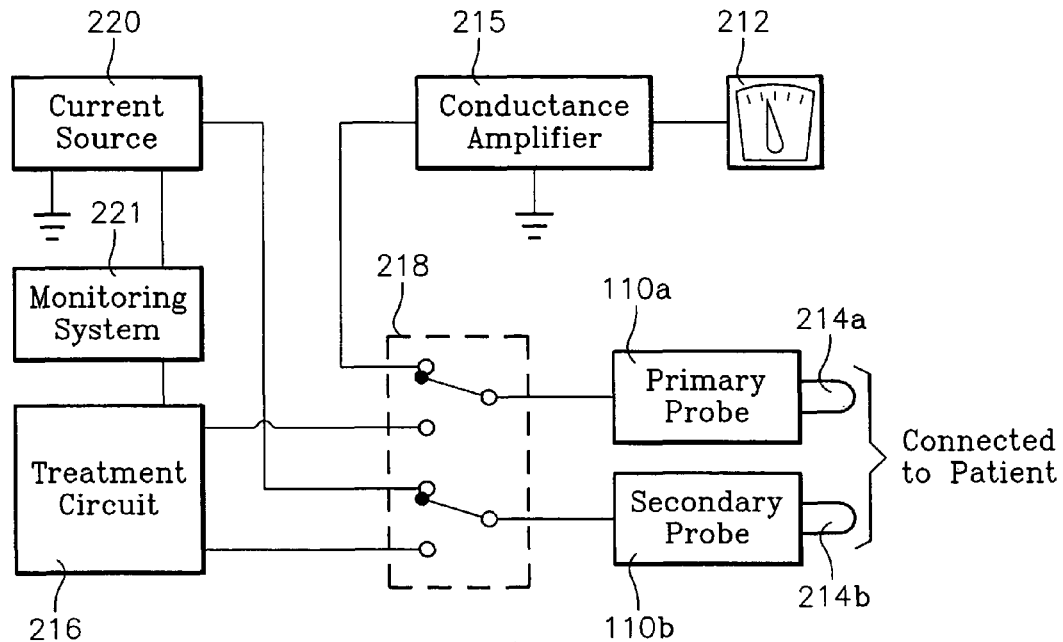
FIG. 2A depicts a schematic diagram of one embodiment of the conduction/impedance measurement circuit (FIG. 2A) of the electronic pain treatment device of FIG. 1.

The electronic pain treatment device of the present invention, combined with its method of application, provides an effective, lasting and non-surgical means of treating pain. FIG. 1 shows an embodiment of the electronic pain treatment device 100 which administers electrical energy, of a specific electrical waveform and generated by the device, to trigger points of the human body associated with the pain. The electronic pain treatment device of the present invention is useful for the treatment of pain including, but not limited to, acute, chronic and post-surgical pain. As shown in FIGS. 2A & B, an embodiment of the invention comprises a variable wave generator 202, an impedance or conductivity measurement circuit 204, a minimum of two electrode probes 110a,b (or a single multi-electrode probe) and various controls and accessory equipment, including an amplitude control 208a, b and a polarity control 209.

Trigger points are discrete, focal, hyperirritable spots located in a taut band of skeletal muscle. They produce pain locally and in a referred pattern and often accompany chronic musculoskeletal disorders. Acute trauma or repetitive microtrauma may lead to the development of stress on muscle fibers and the formation of trigger points. Patients may have regional, persistent pain resulting in a decreased range of motion in the affected muscles. Palpation of a hypersensitive bundle or nodule of muscle fiber of harder than normal consistency is the physical finding typically associated with a trigger point. Palpation of the trigger point will elicit pain directly over the affected area and/or cause radiation of pain toward a zone of reference and a local twitch response. Every muscle has a potential trigger point. When this trigger point flares up, goes into spasm and becomes painful, often that one trigger point radiates its pain to another, satellite point. The combination of the trigger point and satellite point are referred to as a set of trigger points. A more complete description and mapping of trigger points can be found in *Myofascial Pain and Dysfunction: The Trigger Point Manual* by Travell and Simons (Waverly Press, 1983).

Figure 5A:
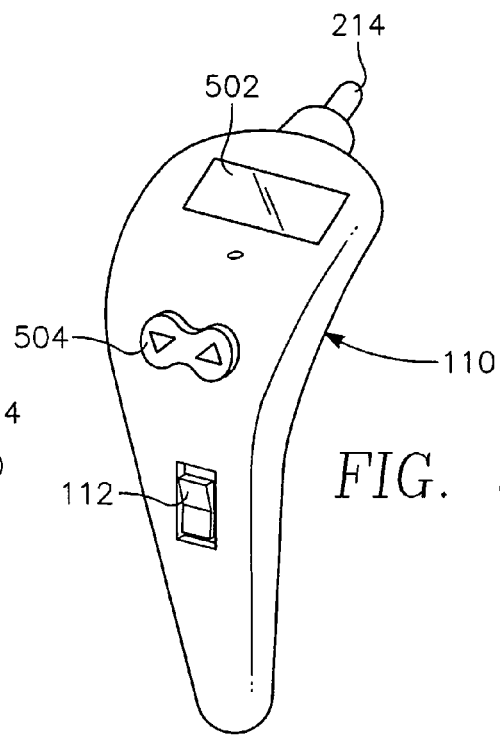
FIGS. 5A-C depict a multi-function probe assembly of the electronic pain treatment device of FIG. 1.
Figure 5B:
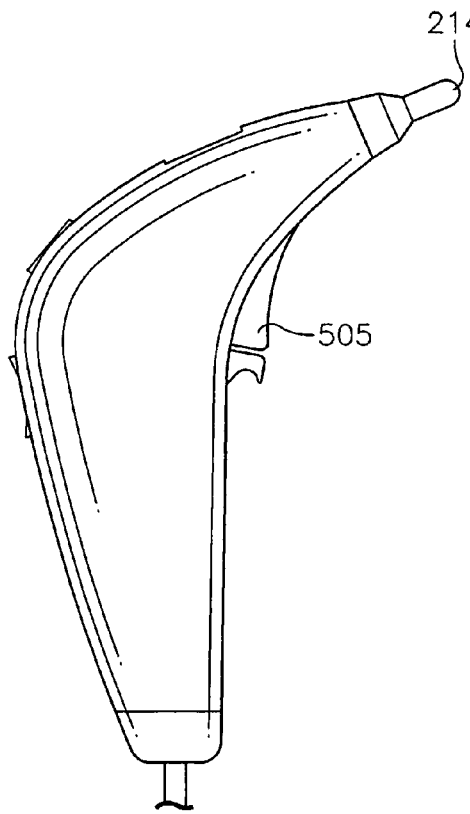
Figure 5C:
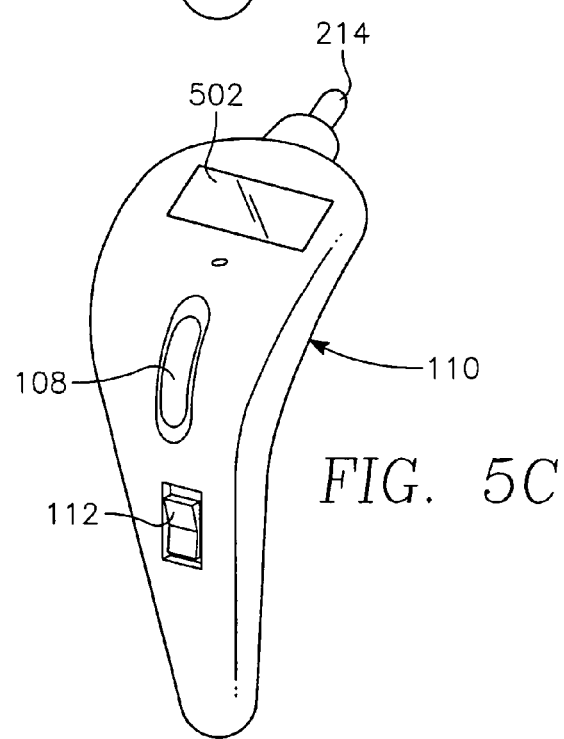

The electronic pain treatment device of the present invention 100 can take various forms. Exemplary, non-limiting examples include: (1) a main console 114 with at least two electrode probes 110a,b that connect to the console via a wired or wireless connection (see, for example, FIG. 1), and optionally one or more remote controls 116 that connect to the console via a wired or wireless connection; (2) a set of probes connected to each other with a wired or wireless connection, and optionally one or more remote controls that connect to the probes in a wired or wireless fashion, but no main console (see, for example, FIGS. 5A-C); and (3) a single, self-contained compound probe assembly (see, for example, FIGS. 6-8) and optionally one or more remote controls that connect to the probe assembly via a wired or wireless connection.

Figure 6:
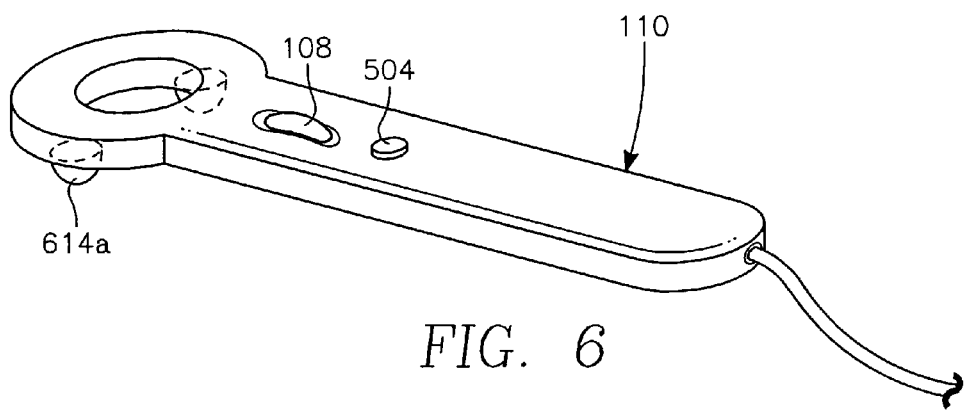
FIGS. 6 and 7 depict a compound probe assemblies of the of the electronic pain treatment device of FIG. 1.
Figure 7:
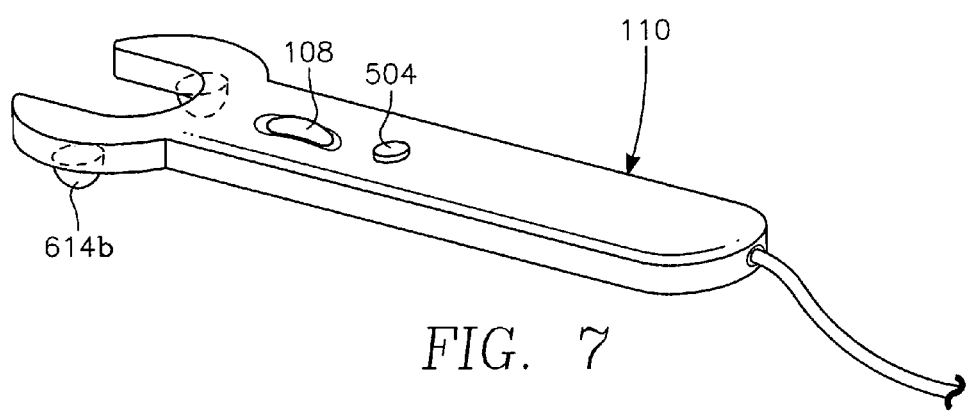
Figure 8:
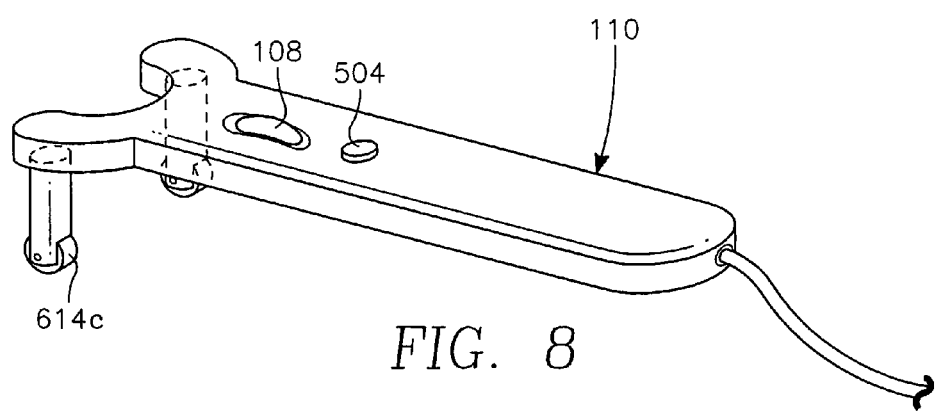
FIG. 8 depicts a roller type probe assembly of the electronic pain treatment device of FIG. 1.

The compound probe assemblies of FIGS. 6-8 having electrodes 614a-c may or may not be self-contained and are useful for treating pain in specific local areas with or without precisely locating trigger points. Such probe assemblies may be used to treat small areas that are presenting pain, or as a local pain reduction device when giving injections, making incisions, or other painful procedures (see FIGS. 6-8 for probe providing opening for injections). This assembly (or the probes described above) may also be moved along a painful area while the device is in treatment mode in order to treat large, painful areas. For example, the electrodes could be moved along a wound or incision that is healing in order to reduce the associated post-operative pain. In an embodiment, the electronic pain treatment device of the present invention 100 can be used as described above to reduce pain in innervated tissues such as tissues having inflammation, bruising or swelling associated with injuries or surgery.

Figure 2B:
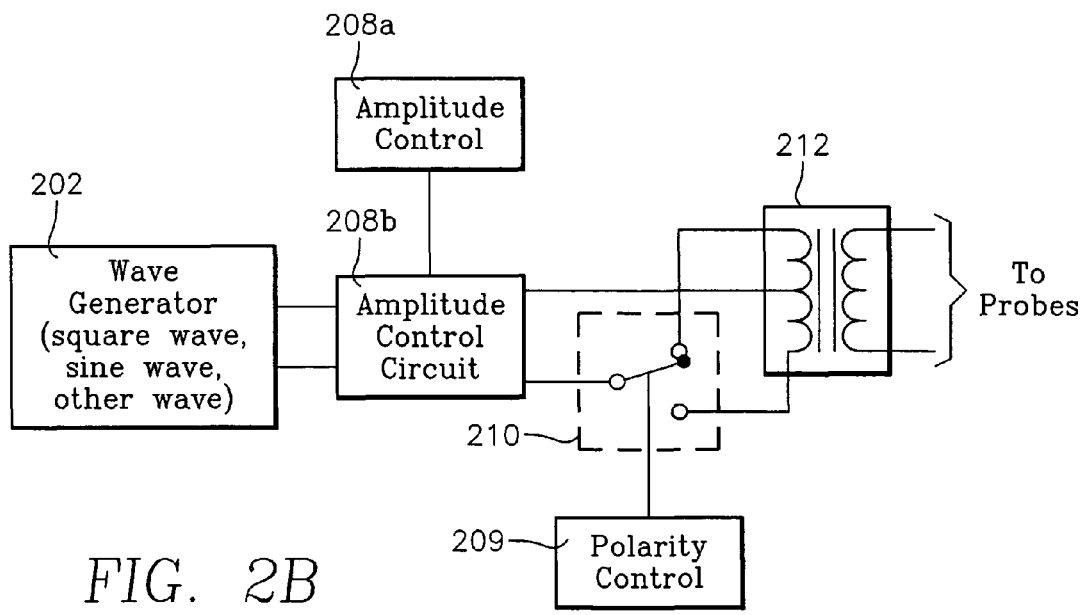
FIG. 2B depicts a schematic diagram of one embodiment of the treatment output circuit (FIG. 2B) of the electronic pain treatment device of FIG. 1.
Figure 3A:
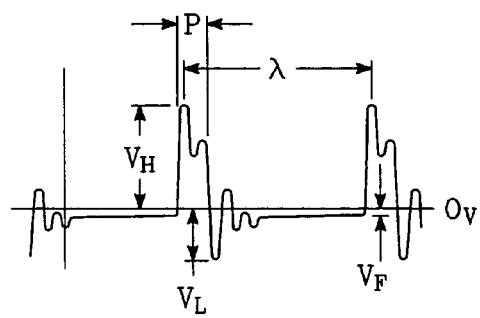
FIGS. 3A-J depict electrical waveforms of the treatment output of the electronic pain treatment device of FIG. 1.
Figure 3B:
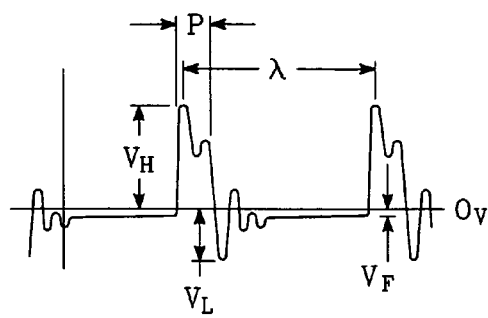
Figure 3C:
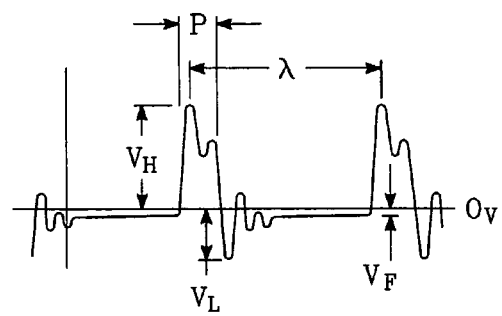
Figure 3D:
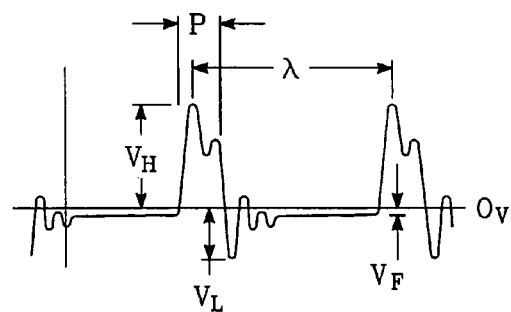
Figure 3E:
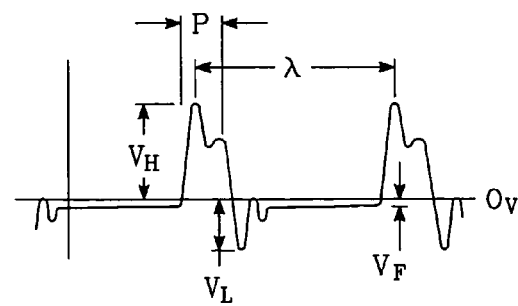
Figure 3F:
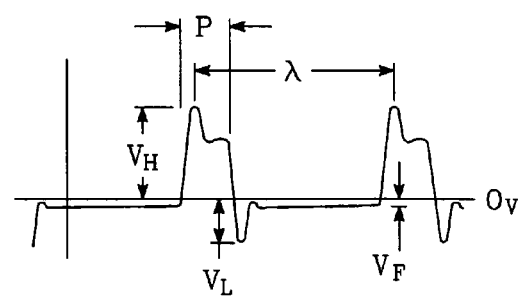
Figure 3G:
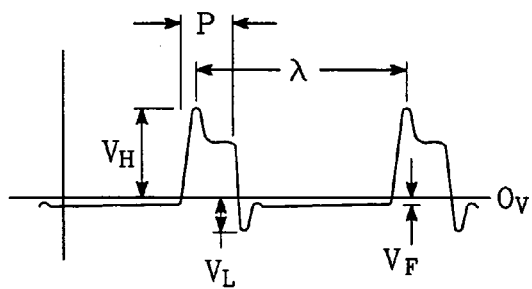
Figure 3H:
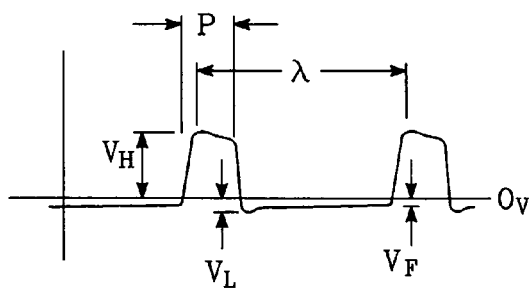
Figure 3I:
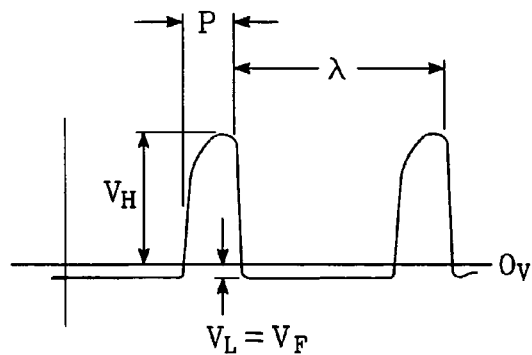
Figure 3J:
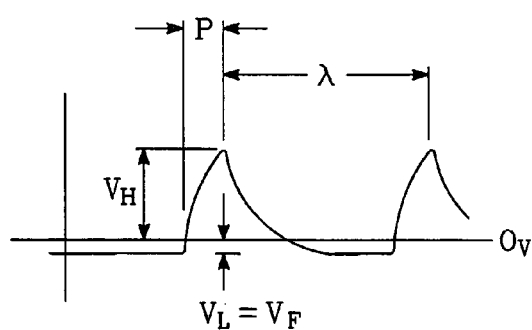

In an embodiment, the electronic pain treatment device of the present invention 100 administers therapeutic electrical energy, of specific and predetermined electrical waveforms, generated by the device, to trigger points associated with the pain. And in some embodiments of the device of the present invention, the device incorporates at least two probes. And in an embodiment, one probe, referred to here as the primary probe 110a, includes a control 112 that signals activation of the therapeutic electrical output as well as other controls 108, indicators, and/or displays 504. In an embodiment, a "trigger" type switch 505 is used to activate the therapeutic output. The second probe is referred to here as the secondary probe 110b. The probes and probe tips 214a, b are of a specific form that is designed to comfortably focus the electrical energy on the trigger points. Because it has been discovered that the facility to reverse the polarity of the electrical output is desirable, the device is configured such that the probe electrical polarity can be reversed enabling both points within the trigger point set targeted for treatment to be treated equally without the need to physically reverse the probes. As shown in FIG. 2B, an embodiment of the invention utilizes a center tapped transformer 212 in combination with a SPDT switch activated by a polarity control 209 to accomplish this function. Other embodiments of this polarity selection feature will also be known to persons of ordinary skill in the art; for example, a DPDT switch could also be used.

In an embodiment of the electronic pain treatment device of the present invention 100, the device has three active modes. First is the "idle mode" wherein the device is active but does not provide electrical output to the probes. The second mode is a "measurement mode" or a "reading mode" wherein a small amount of electrical current is administered between the probes to measure conductivity of innervated tissue, such as human tissue, between the probes. The third mode is a "treatment mode" wherein the electrical wave shape and amplitude (i.e., waveform) available at the probe tips 214a, b are sufficient to be therapeutically effective in treating pain. In alternative embodiments, measurements are taken or not taken when in "treatment mode."

In one embodiment of the electronic pain treatment device of the present invention 100, treatment progress is monitored via a conductivity indication such as from a meter or conductivity indicating device 212 indicating conductivity, resistance or impedance that is incorporated into the device. When in measurement mode, the electronic pain treatment device administers a small direct or alternating current between the probe tips or electrodes 214a, b and utilizes ratios between indicated voltage and current to provide an indication of the conductivity, such as impedance, of the tissue between the probe tips. Typically, before any treatment is applied, the tissue conductivity in the painful area is measured and noted. As treatment proceeds, additional conductivity measurements are periodically taken, and increases in tissue conductivity are expected. Increased conductivity is a consistent marker for immediate reductions in perceived pain. The goal of treatment is to maximize conductivity (minimize impedance) and, as the treatment progresses, to achieve persistent high conductivity measurements. For example, where the electrodes are spaced apart by about 50 mm, initial conductivity measurements in the range of about $1 \times 10^{-8}$ to $1 \times 10^{-7}$ Mhos may be expected, depending on the area being treated. And, during the course of treatment, conductivity increases in the range of about 20 to 500% may be expected, depending on the area being treated. As a person of ordinary skill in the art will recognize, the type and state of tissue being treated and the spacing between the electrodes may result in different ranges; for example, electrodes which are more closely spaced will likely result in higher conductivity readings.

Once the conductivity is maintained at the higher level for a predetermined period of time, the treatment session is concluded for that trigger point set. In an embodiment, time periods indicating the desired persistence of higher conductivity indications are typically in the range of about 5 to 20 seconds. Such persistence indicates that the treatment will alleviate the pain for a substantial time period discussed more fully below. During a single treatment session, a single trigger point set may be treated or a plurality of trigger point sets may be treated.

Figure 4:
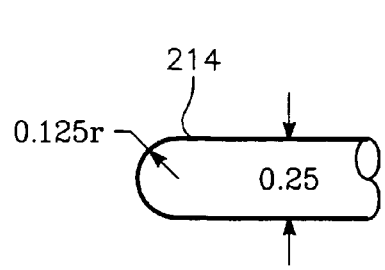
FIG. 4 depicts a probe tip of the electronic pain treatment device of FIG. 1.

The probe tips 214a, b are made of a conductive material such as stainless steel or another conductive metal, non-metal or a matrix including one or both such as a carbon fiber matrix. In an embodiment, the probe tip is a small, rounded tip to allow focused application of the electrical signal. In another embodiment, the probe includes a hemispherical tip with a radius of about 0.125 inches (see also FIG. 4). In yet other embodiments the radius may vary between 0.100 and 0.500 inches. And in some embodiments, an electrode incorporates a conductive roller or wheel 614c allowing the probe to be moved easily along a painful area such as alongside the site of an incision.

The conductance/impedance measurement circuit and/or amplifier 215 and treatment circuit 216 of the electronic pain treatment device of the present invention 100 are depicted in FIGS. 2A and 2B. In an embodiment, the indications of conductance or impedance may be taken when the double pole, double throw (DPDT) switch 218 interconnects the primary probe 110a with the conductance/impedance measurement circuit 215 and interconnects the secondary probe with a current source 220 (as shown). And when the DPDT switch is in an alternate setting, the primary probe is interconnected with the treatment circuit 216 and the secondary probe is interconnected with the treatment circuit.

The electrical output of the electronic pain treatment device of the present invention 100 comprises specific electrical wave shapes of variable amplitude. In an embodiment, the wave shape is akin to a pulse whose shape changes as a function of the impedance of the skin or other tissue under treatment (material between the electrode probe tip 214a, b). FIGS. 3A-J represent a series of waveforms or pulses generated by an embodiment of electronic pain treatment device of the present invention. In this embodiment, the electrodes are placed on the skin of a patient. The highest voltage in the pulse is indicated by $V_H$; the lowest by $V_L$, and the final voltage before the next pulse begins is indicated by $V_F$. The period is indicated by the symbol lambda (λ). The pulse duration is indicated by P. At high impedance (approximately 1 MΩ or more) a first portion of the wave is square-shaped and has two distinct peaks; an adjacent portion of the wave is a damped sinusoid (see, for example, FIG. 3A). As the impedance value reduces, damping of the sinusoidal portion increases (see, for example, FIGS. 3B-3D). At mid-level impedance (approximately 100 KΩ), one of the peaks becomes less distinct and damping of the sinusoidal portion is increased (see, for example, FIG. 3E). As the impedance value continues to reduce, the first portion of the wave begins to take on the shape of a triangle wave and damping of the sinusoidal portion is increased (see, for example, FIGS. 3F-3I). At low impedance (approximately 5 KΩ or less) the first portion of the wave appears as a triangle wave and the sinusoidal portion of the wave is over-damped (see, for example, FIG. 3j). The frequency of the pulses may be varied from 1 Hertz (Hz) to 10,000 Hz and the peak amplitude of the pulses may be varied from 0 to 500 volts. The pulse duration, P, may be varied from 0 milliseconds up to the output's period (λ), which would vary depending on the frequency of the output in a range from about 0.1 millisecond to 1.0 second.

In another embodiment, the electronic pain treatment device of the present invention 100 has an electrical output with a variable frequency and amplitude but a fixed fundamental wave shape (for example, a square wave). And in some embodiments, the treatment output has a wave shape that varies with impedance to form one or more of or a composition of a staircase wave, triangle wave, or sine wave.

When the therapeutic output is activated, the output can reach the set amplitude and current in a few milliseconds, or it can ramp up to this level more slowly. In an embodiment, the ramp-up time is variable between 20 milliseconds and 10 seconds and in another embodiment between 20 milliseconds and 1 minute. Some embodiments limit the voltage to a range of about 0 to 120 volts and the current to a range of about 0 to 10 milliamps. In order to prevent sudden changes to the electrical output that could occur as a result of sudden changes in tissue conductivity, one embodiment of the treatment circuit 216 of the present invention provides a current change-rate limiter to limit to pre-selected values the maximum rate of current change (measured in milliamps/second). Another embodiment of the treatment circuit 216 of the present invention provides a voltage change-rate limiter to limit to pre-selected values the maximum rate of voltage change (measured in volts/second). And in yet another embodiment of the treatment circuit 216 of the present invention, the maximum rate of current change (milliamps/second) is adjusted downward as the conductivity of the tissue between the electrodes increases. In some embodiments, the maximum rate of current change is inversely proportional to conductivity and in other embodiments the maximum rate of current change is adjusted to limit to predetermined values the power dissipated in the tissue as a function of conductivity.

In an embodiment of the present invention 100, the electrical output when taking impedance readings includes a direct or alternating current signal variable between about 0 and 100 Volts. And in an embodiment, the setting for this electrical output for human tissue is about 5.2 Volts.

When the electrical pain treatment device of the present invention 100 is inactive, it provides no electrical output. When active, but not in treating mode (this is referred to "reading mode" or "measurement mode"), the device's electrical output is a direct or alternating current output that is used to determine the impedance of the tissue or material between the probe tips 214a, b. These readings range from 0 Ohms (shorted probe electrodes) to values approaching infinite Ohms (electrodes with airgap between).

These impedance readings can be displayed in one or more forms, including, but not limited to, a numeric, graphic, other visual, or audible forms. In an embodiment, the output display is located on the main console 102 and in another embodiment on a remote display/output 502, 504. Display scales include one or more of a linear scale such as a linear scale of 0-100, a logarithmic scale, an exponential scale or another suitable scale known in the art. Impedance reading displays include those displayed with discrete units (Ohms, etc.), or on a relative/dimensionless scale. In an embodiment, these readings are sent to a computer for analysis, storage, display, and the like.

Impedance readings are used to determine the state of the tissue under test and/or treatment. A reduction in impedance (increase in conductivity) during or after treatment indicates the treatment is reducing the level of pain perceived by the patient under treatment. In an embodiment, the device takes these impedance readings only when in reading mode, and in another embodiment, the readings are taken only when in treatment mode. In yet another embodiment, the impedance readings may be taken in both modes. In this embodiment, automation of the treatment method is enabled since trending of impedance values during treatment allows for control of the treatment duration. In another embodiment, identification of the shape of the waveform allows identification of the transition of a first portion of the waveform from a square-like wave having two peaks to a triangle-like wave having a single peak which signals the end of the treatment.

Where the device does not take impedance readings when in treatment mode, some embodiments provide a display indicating (numerically and/or graphically) the last reading taken before the device was switched from reading to treatment mode, and/or a series of past readings.

In an embodiment, a counter displays the elapsed time since the device was switched from reading to treatment mode (essentially, "treatment duration"). And in an embodiment, the counter resets automatically when the device is switched back to reading mode. In some embodiments, the counter holds its value when reading and resets before the next treatment begins.

In yet other embodiments of the electronic pain treatment device of the present invention 100, components including, but not limited to, counters and/or data collection devices are included to measure parameters such as, but not limited to, total treatment time during the patient's office visit, total reading time during the patient's office visit, total treatment time during the patient's cumulative course of treatment (numerous doctor visits), total reading time during the patient's cumulative course of treatment (numerous doctor visits), total treatment time over the life of the device, total reading time over the life of the device, total number of treatment sessions over the life of the device, total hours of "switched on" time over the life of the device, the locations of the treatment points where the patient was treated over the cumulative course of treatments (numerous doctor visits), and other patient-specific data.

The data generated by the electronic pain treatment device of the present invention 100 can be stored on a computer in electronic form and used to provide medical professionals involved in the care or evaluation of patients information, including, but not limited to, session summaries, and overall course of treatment summaries. Such summaries are useful for numerous purposes, including but not limited to patient-specific analysis, billing support, and clinical trials. In some embodiments, these data are displayed on the device, printed out, stored, and/or transmitted to other systems.

The electronic pain treatment device of the present invention 100 includes a plurality of control actuators which can be operated by the patient or the device operator (typically, a medical professional), or they may be computer-controlled. The control actuators can take the form of any device known in the art which is effective to control an electrical output, including, but not limited to, one or more of knobs 104, sliders, dials or thumbwheels 108, buttons 106, 504, switches 112 or other similar control actuators actuating controls including one or more of analog switches, digital switches, potentiometers, encoders/decoders, or the like. Control actuators actuate controls suitable for controlling parameters of the electrical output and other interfaces of the electronic pain treatment device of the present invention, including, but not limited to the following.

Frequency Adjustment: adjusts the output signal's frequency across its range.

Amplitude/intensity Adjustment: adjusts the amplitude of the output wave.

Stop Treatment/Amplitude to Zero Control: sets the amplitude to zero when activated.

Volume Adjustment: adjusts the volume of the conductivity reading audio output.

Tone Adjustment: adjusts the tone of the conductivity reading audio output.

Display Adjustment: adjust the intensity/contrast/color/etc. of the electronic pain treatment device's displays.

Polarity Switch, such as a two-position switch or a/b toggle that reverses the polarity of the treatment probes. This has the same effect as switching the probes with each other, but without interrupting the treatment or moving the probes.

Data Interface, such as analog or digital input/output via one or more wired or wireless interfaces such as 802g, USB or ethernet interface.

The above controls can be located in locations on the device including, but not limited to, on the main console 114 of the device; on one of the treatment probes 110 (wireless or non-wireless) or on a remote control 116 (wireless or non-wireless). In an embodiment, certain controls are operated by the device operator and in another embodiment, the same or fewer than the same controls are operated by the patient. And in an embodiment having redundant controls (such as a redundant adjustment control located on the main console, one of the probes, and/or a remote control), a controller incorporated in the device determines which control or control actuator is active. A typical controller includes an A/B or A/B/C, etc. selector switch for providing, inter alia, a scheme whereby all controls are active, a scheme whereby some of the controls are active, and a controller scheme with a hierarchical logic to determine which subset of controls or control actuator is active. In an embodiment, a controller scheme determines that if a remote is present, then the remote control is active and other controls are not; or, if there is no remote present, then the control on the main console is active. In another embodiment of the electronic pain treatment device of the present invention, an indicator to indicate which control is active is present. An exemplary indicator is a lamp or similar light-emitting device. Also, an indicator lamp may be used to indicate whether the treatment is active/on or inactive/off.

In an embodiment, the medical professional may operate all of the controls on the device 100. And in an embodiment, the intensity of the electrical output is selected by the patient (using one or more of the amplitude, frequency, or a combined amplitude and frequency adjustment). Here, the patient is instructed to set the intensity at a point where he or she strongly feels a tingling sensation but is not feeling pain from the treatment; this provides the patient the means to treat the pain aggressively but safely and comfortably (see earlier discussion of current and voltage limiting) while ensuring that future treatments are not suppressed by memories of a painful experience when another operated these controls. Frequency and/or amplitude adjustments that result in the "tingling sensation" vary for different patients. Typically, the frequency adjustment is set in the range of about 1 to 10,000 Hz and the amplitude adjustment is set in the range of about 0 to 500 volts.

In an embodiment, the method of treatment disclosed herein consists of a single treatment session. In yet another embodiment, the method of treatment discussed herein comprises a series of treatment sessions. Notably, the administration of electrical energy as described above has been found to have an unexpected generally cumulative effect. In some embodiments of the method of the present invention, multiple treatment sessions can take place 24-72 hours apart, preferably at least about 24 hours apart.

The number of treatment sessions necessary to treat an individual patient is to be determined by a medical professional. In one non-limiting example, a series of treatment sessions in a range from two to twelve sessions is appropriate. It is also within the scope of the present invention to provide additional treatment sessions, including weekly sessions for a prolonged period of time, months or years or occasional sessions over similar time periods.

During treatment of pain with the electronic pain treatment device of the present invention, communication between the patient and the medical professional is necessary to evaluate the perceptions of comfort of the patient. And, in initiating a treatment session, it is recommended to determine precisely where the pain is; in most cases the patient can be quite specific about the location of the pain. After locating the painful spot or area, the primary probe tip 214a,b is placed on this location (the trigger point) and the secondary probe tip is placed on an associated satellite or involved point. The satellite location is located by locating a second nearby trigger point using the methods discussed herein. When the treatment begins, communication with the patient should continue; the patient should be asked whether they believe the correct location is being treated. Patients often can sense whether the appropriate area is being treated. If the patient is certain the area being treated is not the right area, a different area should be selected for treatment, preferably with the patient's assistance.

When a set of trigger points has been treated, the patient is typically asked whether the treatment seems to have helped. Especially in the first treatment, one of the medical professional's goals is to find those trigger points where treatment is most effective. This can take some time and for that reason the first treatment session in a series of treatments generally requires 25% to 50% more time than subsequent sessions of typically 5 to 15 minutes per trigger point treated.

In most cases, the treatment is carried out on trigger point sets adjacent to or on the site of the painful location. These trigger point sets can be found manually as described above and/or with the aid of the conductivity meter 212. Manually located trigger point locations can also be confirmed by use of the conductivity or impedance indicating meter; for example impedance values obtained from a tissue sample which is not in pain may be compared to impedance values obtained from manually located trigger sets. Locating trigger point sets is thus aided by both conductivity and/or impedance measurements and palpation or application of pressure in painful areas identified by the patient.

A goal of the treatment with the electronic pain treatment device of the present invention 100 is to improve the conductivity of the painful area. An initial conductivity measurement is taken before treatment; then the site is treated for about 1 minute, and the conductivity is measured again. If the conductivity has not increased (impedance decreased), the treatment may not have occurred on the proper points; if so, the probes typically should be relocated as described above. If there is an increase in conductivity, the treatment should continue for about 30 seconds and then the conductivity should be measured again. It may be necessary to adjust the amplitude or frequency of the electrical output to prevent the treatment from becoming uncomfortable for the patient as the tissue's impedance changes. Treatment is continued until the conductivity no longer increases and the conductivity stays at or near the highest achieved level for about 10 seconds. At this time, the pain is reassessed and either the next set of trigger points is identified and treated or, where beneficial, as may be indicated by the patient, the polarity is reversed and treatment of the same trigger points continues.

In an embodiment, after treating a pair of sites with the primary probe on the most painful site and the secondary probe on an adjacent, or satellite site, the probe polarity is reversed (using the polarity switch) and the treatment regime described above continues until conductivity is increased by about 20 to 500% FIG. 2A depicts a schematic diagram of one embodiment of the conduction/impedance measurement circuit (FIG. 2A) and treatment output circuit (FIG. 2B) of the electronic pain treatment device of FIG. 1. This ensures that both sites receive therapeutic treatment.

After treating the initial painful points one may find that the pain has "moved." Patients may indicate that the pain at the first spot has abated and that it has moved to a new, often close by, location. In fact, what has happened is that, once the original painful location has been treated, the patient is now aware of pain that was masked by that of the original painful location. Because of this phenomenon, it is typical to spend time "chasing the pain" around one or more specific areas. It is also typical that chasing the pain occurs less frequently as the course of treatment progresses. As the goal is to eliminate "the pain," the treatment continues while the pain is chased until no further painful locations present themselves. This chasing technique requires frequent communication with the patient.

While the patient may be feeling substantially better at this point, this improvement may or may not persist and it should be expected that additional treatment sessions may be required to eliminate and/or manage the pain. In many treatment regimes, follow-up visit/treatment sessions will be scheduled to occur within 24 to 72 hours from the time of initial treatment session.

While the electronic pain treatment device of the present invention and associated methods of treatment, have thus far been described with regard to its use in a non-invasive manner, it is within the scope of the present invention to use the device, and the associated methods, during surgery, as an implantable device, in wound healing and in other instances. Such other instances include use of the present invention for wound healing, bone healing, macular degeneration and multiple sclerosis.

In another embodiment of the electronic pain treatment device of the present invention 100, a monitoring system 221 is provided to control and/or monitor the usage of the device. The monitoring system is useful to monitor the number of uses of the device including dispensing uses, storing information on uses and storing and obtaining credits for the use of the device. One use can represent different parameters and any of the following types of "use" can be monitored with the monitoring system of the present invention. A use, or one use, may include, but is not limited to, a specific amount of time during which the device is active or enabled, a specific amount of time during which the device is in treatment mode; a specific amount of electrical power used, one complete treatment session, and the like. In an embodiment, uses are quantified and controlled by use credits which are electronic units of use that are purchased enabling operation of the device.

In one embodiment of the present invention, where a "use" is determined by a specific amount of time (for example, active time, enabled time, measurement time, or any combination of these or other parameters), an "extend treatment" function may be employed that enables the user to extend the treatment for a specific amount of time without using an additional use credit. In some embodiments, the "extend treatment" function is used with a cumulative electrical energy administered use-measurement system.

In another embodiment of the present invention, the medical professional who administers treatment using the electronic pain management device 100 purchases use credits which allow the use of the device. For example, the medical professional purchases ten use credits and the monitoring system 221 of the electronic pain treatment device tracks the consumption of these credits. After ten uses of the device, the medical professional is required to purchase additional credits to continue use of the device. The monitoring system thereby limits use of the device to users having use credits.

In yet another embodiment of the present invention, the monitoring system 221 includes systems for controlling the number of uses of the electronic pain treatment device during a particular period of time. In this embodiment of the monitoring system, the medical professional purchases from the device's manufacturer a fixed number of uses as discussed above. A system for storing, tracking and dispensing the uses includes but is not limited to, at least one of the following: card readers such as Smartcards, standard magnetic cards, optical cards, etc.; a plug in dongle or cartridge; a link to a computer system from which credits for use are downloaded; a keypad or other input device; and other devices as are known to those skilled in the art.

Methods for tracking the uses and use credits include but are not limited to, a device, including a remote device or integral device, which displays the number of use credits available to the user of the device, a printed document which displays the number of available use credits, a computer-based system which displays and tracks the number and use of use credits.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation present in their related test measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventor intends for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

It is also to be understood that the embodiments of the invention disclosed herein are illustrative of the principles of the present invention. Other modifications that may be employed by persons of ordinary skill in the art are within the scope of the invention. Thus, by way of example, but not of limitation, alternative configurations of the present invention may be utilized in accordance with the teachings herein. Accordingly, the present invention is not limited to that precisely as shown and described, but is that which is described by the appended claims.

EXAMPLE

A group of forty patients experiencing chronic pain have received cutaneously administered treatment using an embodiment of the device and method of the present invention. The device included probes, a treatment circuit and an impedance measurement circuit. Pain levels indicated by relative impedance were recorded using a 100 mm Visual Analog Scale (VAS).

The treatment methodology for all patients included assessment of patient pain level, initial location of trigger point sets, placement of the probes on the trigger points, initial or base line impedance measurements (inverse of conductivity), administering the therapeutic output, measuring impedance, and receiving patient feedback.

The assessment of patient pain level prior to treatment was done using the 100 mm Visual Analog Scale, where the patient marked his or her own pain level along the 100 mm scale with values of 0 representing "no pain" and 100 representing "the worst pain imaginable." A typical pain level for untreated patients was 70 mm.

Locating trigger points began with the patient's indication of the painful area. Palpation by the medical professional was used to confirm the general location and also to locate the most painful spot within that area. Continued palpation in the region around the trigger point was used in conjunction with patient feedback to locate a satellite point or second nearby trigger point. Having located the trigger point set, a first probe was placed on one trigger point and a second probe was placed on the other trigger or satellite point.

The initial or baseline impedance was measured by applying a DC voltage of between 2 and 10 volts to establish a current flow through the tissue between two electrodes. From this, the impedance measurement circuit calculated the impedance of the tissue between the electrodes and displayed a relative indication on the display.

Initially, the therapeutic output of the device was set to administer a series of pulses at a frequency in the range of 450 to 500 pulses per second. The voltage was adjusted from zero upwards until the patient perceived a tingling sensation, generally in the range of 0 to 120 volts. The therapeutic output so adjusted was applied for about 60 seconds. If the treatment begins to become more painful for the patient, the voltage and/or frequency was adjusted to ensure that discomfort was minimized.

Impedance measurements were made following the initial application and typically showed a reduction in impedance. The goal of the treatment during each patient visit was to decrease the impedance (increase the conductivity) through successive applications of the therapeutic output to achieve a persistently (5 to 20 seconds) lower level of impedance. When successive treatments showed little or no impedance change, the patient's treatment session for that office visit was ended, or in cases, a second set of trigger points was treated.

Because it was found that the effects of multiple treatments were cumulative, patients were treated in multiple office visits and some patients made as many as twelve such visits for treatment. Patient feedback confirmed a strong correlation between the reduction of perceived pain and a decrease in impedance. For each patient, a pain assessment was taken one week after that patient's last treatment session; on average the entire group measured 35 mm on the VAS. Fifteen of these patients had individual VAS indications of under 10 mm. For several patients, the relief from pain persisted for months following their last treatment session.

I claim:

1. An electronic pain treatment device for treating tissue of a human patient associated with pain, comprising:
    a main console;
    a first circuit in the main console and operable to measure, in a measurement mode, an impedance associated with painful innervated tissue of the human patient;

a display on the main console receiving signals from the first circuit, the display providing a quantitative indication of the impedance;

first and second electrodes operable to supply electrical energy to and to receive electrical energy from an area of tissue of a patient associated with pain, the first and second electrodes each including corresponding probe tips that are made of a conductive metal and that have a hemispherical tip, the first and second electrodes connecting to the main console via separate respective wired connections such that the first electrode can be positioned at different and variable locations on the patient relative to the second electrode, wherein the first electrode is movable independently of the second electrode;

a treatment circuit in the main console that includes a variable wave generator that generates the electrical energy in the form of electrical waveforms of variable frequency and variable amplitude in a treatment mode by supplying the electrical energy as pulses having a fixed polarity and a variable frequency up to on the order of thousands of Hertz;

a switch accessible from the main console for selectively electrically interconnecting said electrodes with said first circuit and causing thereby a quantitative measurement of the severity of pain of the innervated tissue by said first circuit in the measurement mode and for selectively interconnecting said electrodes with said treatment circuit and causing thereby the electrical waveforms to be supplied to the innervated tissue by said treatment circuit in the treatment mode;

a current limiter in the main console for limiting the rate of increase of current generated by the treatment circuit to a pre-selected value;

a probe connected to the first electrode;

a control for varying the amplitude of the electrical waveforms generated by the treatment circuit as the treatment circuit is generating the electrical waveforms;

a counter on the main console that displays an elapsed treatment time indicative of the time that the electrical waveforms are supplied to the electrodes in the treatment mode; and a monitoring system to control or monitor a use of the device, wherein the use includes the elapsed treatment time.

2. The device of claim 1 further comprising a voltage limiter for limiting the rate of increase of voltage generated by the treatment circuit to a pre-selected value.

3. The device of claim 2 further comprising means for adjusting the rate of current increase as a function of one or more of said measured impedances.

4. The device of claim 2, further comprising:
a second display integral with said probe.

5. The device of claim 1 further comprising a second display integral with said probe.

6. The device of claim 1 further comprising a polarity switch for reversing the polarity of the two electrodes.

7. The device of claim 1 further comprising a totalizer for deactivating the device when a pre-determined totalization of at least one of device time of use or device energy consumed is reached.

8. The device of claim 1, wherein the electrical energy received by the electrodes is a direct current.

9. The device of claim 1, further comprising means for reversing the polarity of the pulses.

10. The device of claim 1, wherein the monitoring system includes a plug-in dongle for storing, tracking, and dispensing use credits.

11. The device of claim 1, wherein the use further includes an amount of time during which the device is active, an amount of time electrical power is used by the device, or a complete treatment session.

12. The device of claim 1, wherein the control comprises a remote control adapted to be operated by the patient.

13. The device of claim 1, wherein the control is integral with the probe.

14. The device of claim 1, wherein the area corresponds to discrete, focal, hyperirritable spots located in a taut band of skeletal muscle of the patient.

15. The device of claim 1, wherein the main console includes the control.

16. The device of claim 1, wherein the variable frequency is adjustable from 1 Hertz up to 10,000 Hertz.

17. The device of claim 1, further comprising a data collection device that stores information indicative of the locations of treatment points where the electrodes were placed on trigger points over a course of treatments.

18. The device of claim 1, wherein the treatment circuit is configured to determine the time period during which the variable waveform generator supplies the electrical energy to the innervated tissue in the treatment mode.

19. The device of claim 1, wherein a radius of the probe tips is between 0.1 and 0.5 inches.

20. The device of claim 19, wherein the radius is about 0.125 inches.

21. The device of claim 1, the peak amplitude of the electrical waveforms is variable by the control from 0 to 120 Volts or from 0 to 500 Volts.

* * * * *